(12) United States Patent
Peters et al.

(10) Patent No.: US 7,524,295 B1
(45) Date of Patent: Apr. 28, 2009

(54) CONVERTIBLE ANKLE BRACE

(75) Inventors: Rick Peters, Indianapolis, IN (US); Randolph Smith, Indianapolis, IN (US); Tony Parker, Greenfield, IN (US); Matt Haws, Noblesville, IN (US)

(73) Assignee: Ultra Athlete LLC, Indianapolis, IN (US)

( * ) Notice: Subject to any disclaimer, the term of this patent is extended or adjusted under 35 U.S.C. 154(b) by 10 days.

(21) Appl. No.: 11/767,806

(22) Filed: Jun. 25, 2007

(51) Int. Cl.
*A61F 5/00* (2006.01)

(52) U.S. Cl. .............................. 602/5; 602/23; 602/27
(58) Field of Classification Search .............. 602/5, 602/23, 26, 27; 128/882
See application file for complete search history.

(56) References Cited

U.S. PATENT DOCUMENTS

| | | | |
|---|---|---|---|
| 582,192 A * | 5/1897 | Entrekin ..................... 602/16 |
| 4,834,078 A | 5/1989 | Biedermann | |
| 5,069,202 A | 12/1991 | Prock | |
| 5,209,722 A | 5/1993 | Miklaus et al. | |
| 5,902,259 A | 5/1999 | Wilkerson | |
| 6,053,884 A | 4/2000 | Peters | |
| 6,129,695 A | 10/2000 | Peters et al. | |
| 6,524,266 B1 | 2/2003 | Peters | |
| 6,602,215 B1 | 8/2003 | Richie, Jr. | |
| 6,689,081 B2 | 2/2004 | Bowman | |
| 6,749,578 B2 | 6/2004 | Peters | |
| 6,767,332 B1 | 7/2004 | Pardue et al. | |
| 6,858,017 B2 | 2/2005 | Peters | |
| 6,955,654 B2 * | 10/2005 | Gilmour ..................... 602/16 |
| 6,969,363 B2 * | 11/2005 | Houser ....................... 602/16 |
| 7,018,352 B2 | 3/2006 | Pressman et al. | |

* cited by examiner

*Primary Examiner*—Michael A. Brown
(74) *Attorney, Agent, or Firm*—Camoriano and Associates; Theresa Fritz Camoriano

(57) ABSTRACT

An ankle brace may be convertible so it can be used at various stages of treatment, from functioning as a splint when the ankle is first injured, to functioning as a pivoting, relatively non-restrictive protective brace after the ankle has fully healed. The brace also may have a pivoting buckle with the range of pivoting motion of the buckle being limited to provide for the brace to adapt to the wearer while still providing stability and support.

18 Claims, 10 Drawing Sheets

CONVERTIBLE ANKLE BRACE

BACKGROUND

The present invention relates to an ankle brace. More particularly, it relates to an ankle brace which can be adjusted to perform different functions, depending upon the needs of the wearer. It may serve either as a protective brace, which limits the range of side-to-side foot motion during normal athletic activities, or as a therapeutic ankle orthosis during the transitional period between resolution of acute sprain symptoms and complete restoration of normal ankle function.

Traditionally, ankle braces have been designed either to help prevent an ankle injury or to protect an existing acute ankle injury. The ankle braces designed to prevent an ankle injury are smaller in scale, usually made out of a flexible material such as cloth, and only provide minimal support. Those ankle braces designed to protect an acute ankle injury are larger in scale, usually made out of a rigid material, such as a plastic, and provide maximum support.

A functional ankle brace designed to prevent an ankle injury would not be used to protect an acutely injured ankle, because it lacks the necessary support and stability. A therapeutic ankle orthosis designed to protect an acute ankle injury would not be used for prevention, because it would be bulky, cumbersome, and restrict too much mobility.

SUMMARY

Certain embodiments of the present invention allow the user to convert an ankle brace to perform different functions, so it can be used first to treat an acutely injured ankle and then, after the ankle has healed, it can be used during normal athletic activities to protect against future injury.

One embodiment provides a snap-fit, upright extension which attaches to a "basic" (or functional) brace to provide an increased level of support and stability. With this upright extension, the brace is taller and provides more support.

Another embodiment provides a guide for cutting off the top portion of the brace to make it shorter and to provide for greater mobility once the ankle has healed.

Another embodiment provides a snap-fit, range-of-motion lock to the "basic" brace which fixes (locks) the brace in a neutral position to act as a splint. This splinting effect immobilizes the ankle, which is recommended for acute angle injuries for the first 24 to 48 hours after the injury. When swelling and pain have decreased to a point that rehabilitation can start, the range-of-motion lock can be detached from the brace allowing full plantar and dorsiflection of the ankle. Should immobilization be needed again, the range-of-motion lock can be reattached.

Another embodiment provides an ankle brace having strap buckles with limited rotation capability. Most ankle braces have a fixed buckle or slot to receive a strap to secure the brace to the leg, providing no capability for the strap to adjust to the angle and anatomy of the leg. A fully rotating buckle, on the other hand, provides excellent strap alignment with the leg, but full rotation also means unlimited motion between the buckle and the body of the brace, resulting in a lack of stability. A brace with a buckle which offers limited rotational capabilities allows the strap to efficiently fit the anatomy of the lower leg while still providing good support.

DESCRIPTION

Figure 1:
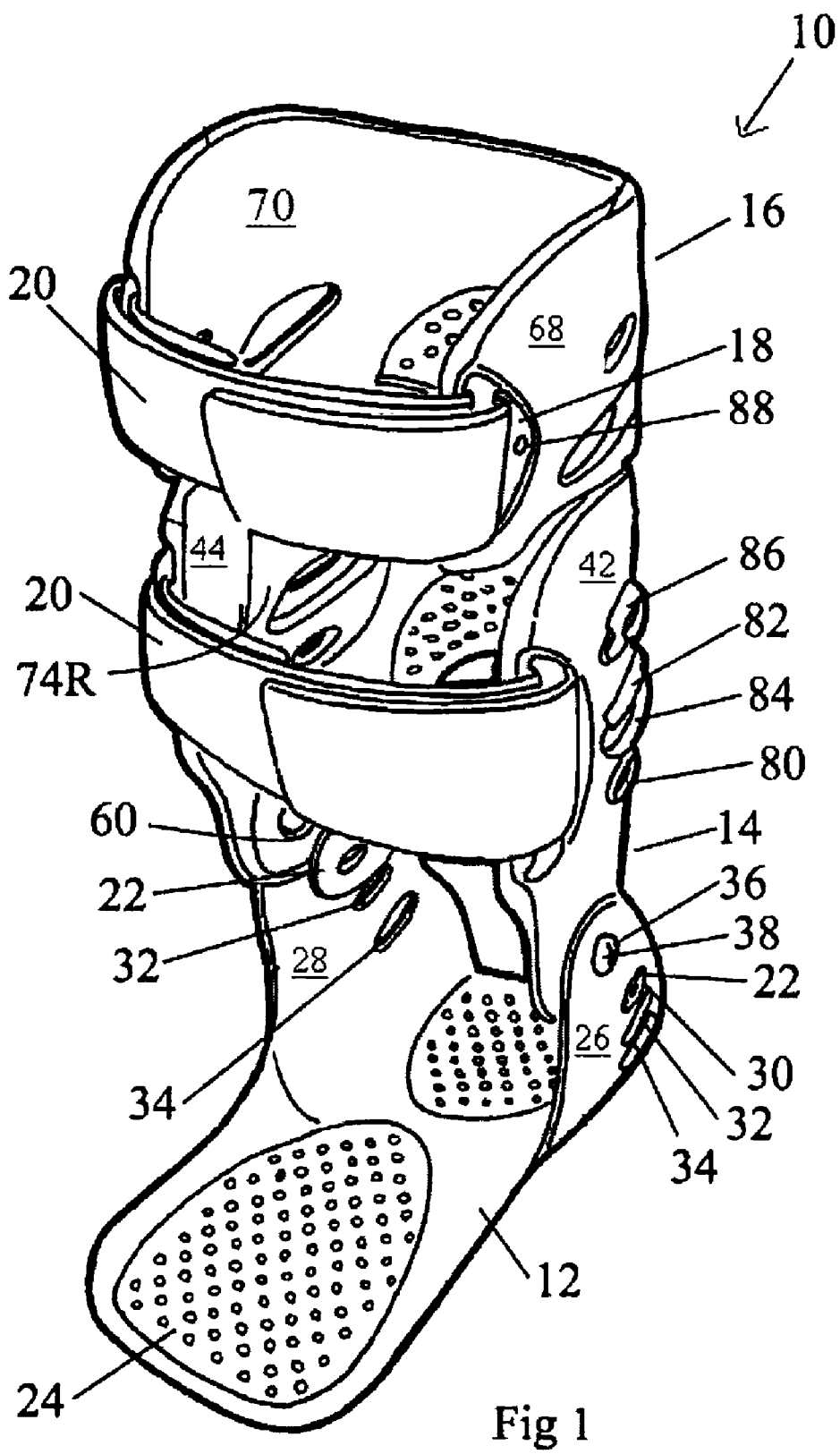
FIG. 1 is a perspective view of an ankle brace made in accordance with the present invention.
Figure 2:
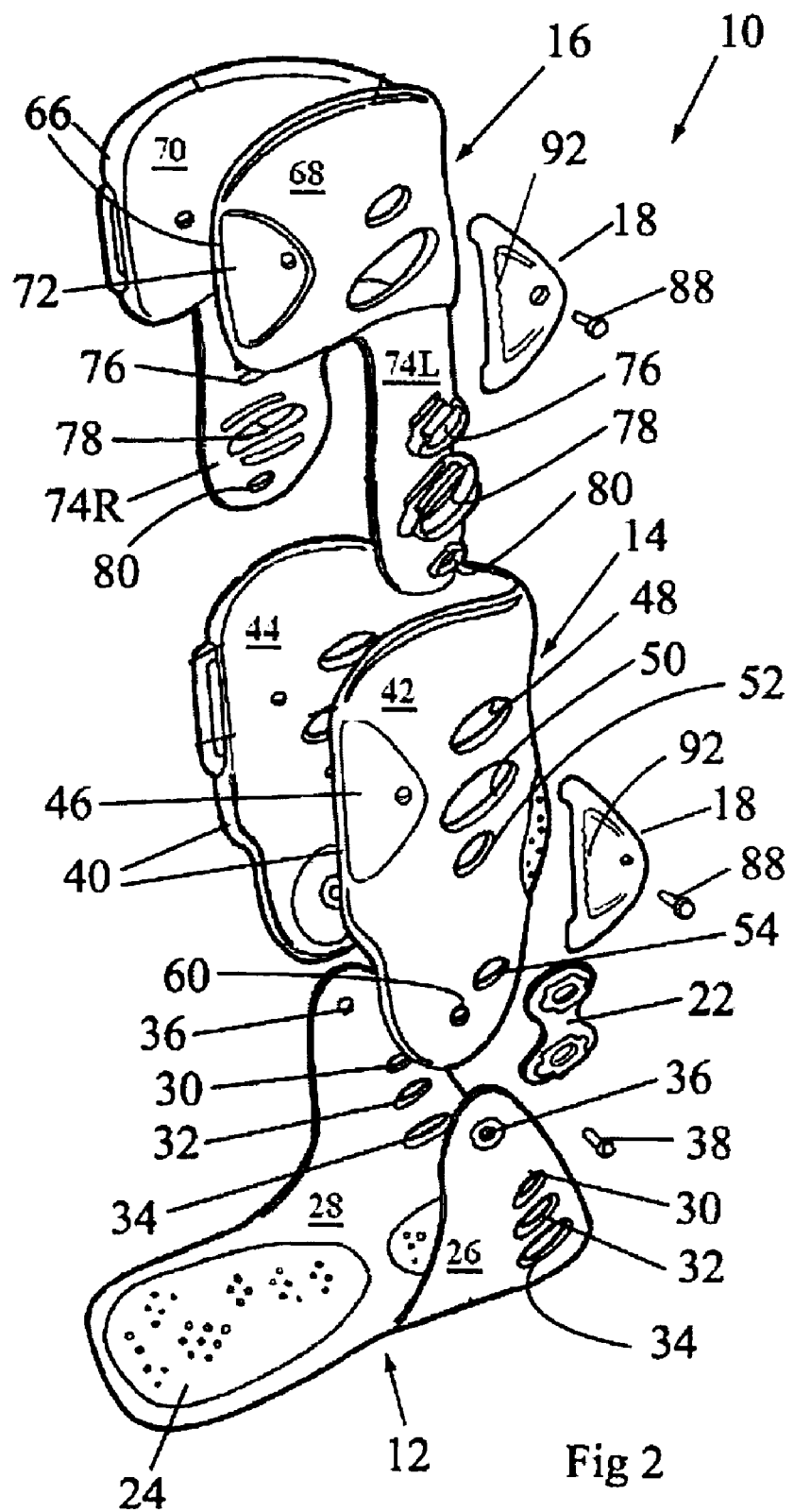
FIG. 2 is an exploded, perspective view of the ankle brace of FIG. 1, with the straps removed for clarity.

FIGS. 1-6 show an ankle brace 10 made in accordance with the present invention. Referring to FIGS. 1 and 2, the ankle brace 10 includes a foot shell 12, a medial shell 14, an upright extension shell 16, limited rotation buckles 18, straps 20, and range-of-motion locks 22.

The foot shell or stirrup 12 includes a base portion that underlies the foot (not shown) and includes a substantially flat extension 24 which projects forward to just beyond the arch of the foot. The foot shell 12 has a contoured stirrup shape and includes left and right upper side portions 26, 28, respectively. Each of these upper side portions 26, 28 defines a series of substantially oval-shaped through openings 30, 32, 34 (See also FIG. 3), at least one of which cooperates with a snap fit, range-of-motion lock 22 as described in more detail below.

The medial shell 14 has a substantially "U" shaped cross section and is designed to fit against, and is contoured to, both lateral sides and the posterior side of the lower leg and ankle, and is open at the anterior side 40. Adjacent the anterior side 40, and on the outer surface of both lateral walls 42, 44 of the medial shell 14, are triangularly-shaped indentations 46, designed to engage similarly shaped buckles 18 to allow limited rotation of the buckles 18 as explained in more detail below.

The medial side portions 26, 28 of the foot shell 12 overlap the medial shell 14 such that rivets 38 extending through openings 36 (in the foot shell 12) and 60 (in the medial shell 14) pivotably secure the foot shell 12 to the medial shell 14.

The lateral walls 42, 44 also define a series of substantially vertically aligned, oval-shaped through openings 48, 50, 52 (See also FIG. 3) which engage a snap-fit, upright extension shell 16 attachment as described in more detail below. An additional through-opening 54 adjacent the lower end of each of the lateral walls 42, 44 of the medial shell 14 (and located to the rear of the through opening 60 which defines the pivot point between the medial shell 14 and the foot shell 12) is used, in cooperation with a respective range-of-motion lock 22 and at least one of the openings 30, 32, 34 in the foot shell 12, to lock the foot shell 12 against pivoting motion relative to the medial shell 14, as described in more detail below.

Figure 6:
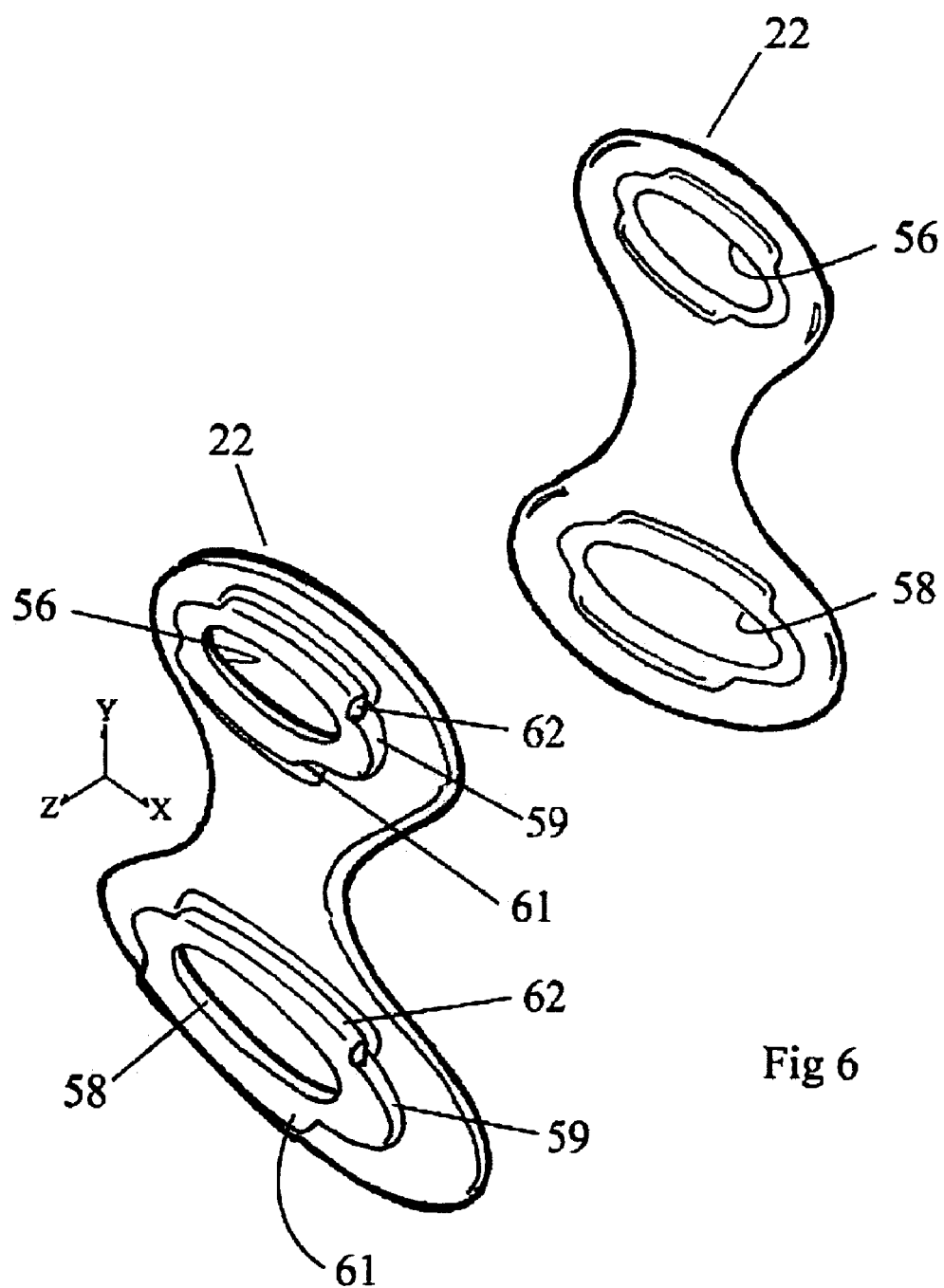
FIG. 6 is a perspective view of the Range-Of-Motion locks of the ankle brace of FIG. 1.
Figure 6A:
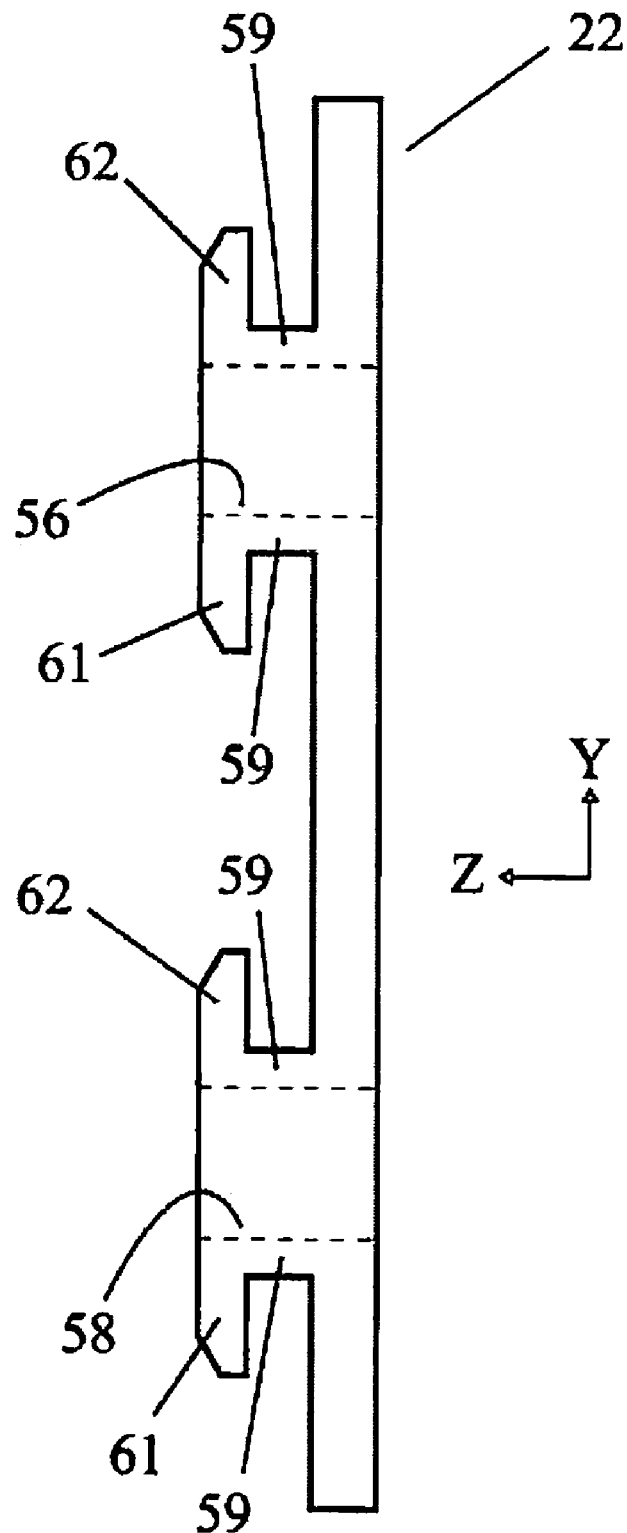
FIG. 6A is a front view of one of the Range-Of-Motion locks of FIG. 6.

FIGS. 6 and 6A depict the range-of-motion locks 22, which are identical. Each range-of-motion lock 22 is substantially figure-8 shaped and defines upper and lower oval-shaped through openings 56, 58, elongated in the "x" direction (see FIG. 6), with each opening 56, 58 surrounded by a raised oval insert 59 projecting outwardly in the "z" direction, and with raised flanges 61, 62 projecting upwardly and downwardly in the "y" direction, respectively. The raised flanges 61, 62 are tapered on their outer surfaces to facilitate their insertion into the oval openings 54, 30 of the medial shell 14 and foot shell 12, respectively, and they are flat on their rear surfaces. These raised flanges 61, 62 are flexible enough to snap through their respective openings 30 (in the foot shell 12) and 54 (in the medial shell 14) to releasably lock onto the foot shell 12 and medial shell 14, respectively, to prevent relative pivoting motion of the foot shell 12 and medial shell 14 about the rivets 38.

To summarize, the raised oval inserts 59 act as projections which extend outwardly through the opening 30 in the foot shell 12 and the opening 54 in the medial shell 14, and the flanges 61, 62 act as deformable "hooks" at the end of these projections 59, abutting the outer surfaces of the foot shell 12 and medial shell 14 to secure the range-of-motion locks 22 to the foot shell 12 and the medial shell 14 a the openings 30, 54. When the range-of-motion locks 22 are snapped into the brace 10 to restrict pivoting movement between the foot shell 12 and the medial shell 14, the brace 10 acts as a splint.

Figure 5:
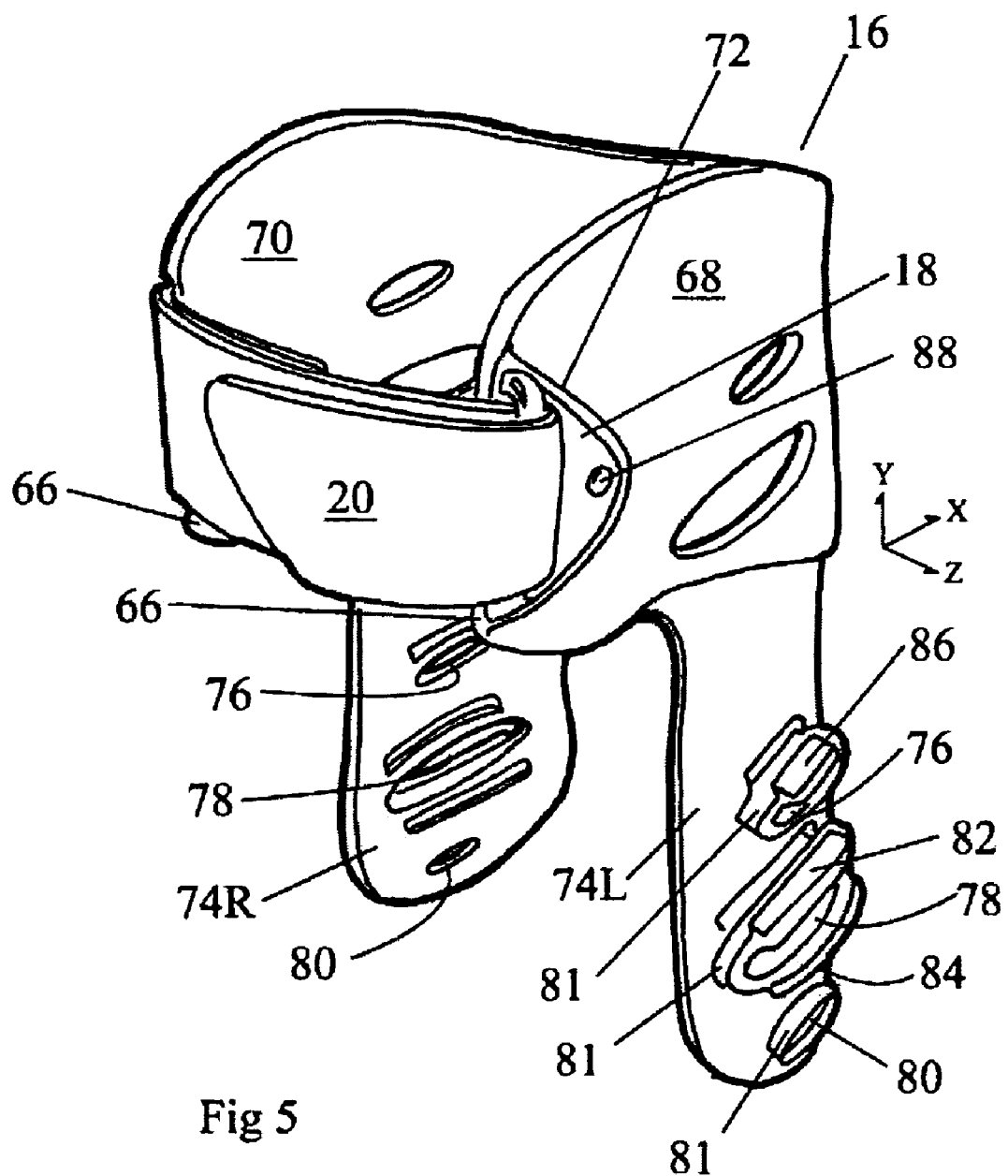
FIG. 5 is a perspective view of the upper extension shell of the of the ankle brace of FIG. 1.

Referring now to FIGS. 2 and 5, the upper extension shell 16 also has a substantially "U" shaped cross section, similar to the medial shell 14. On the outer surface of the upper extension shell 16 on both lateral walls 68, 70 adjacent the anterior side 66 are triangularly-shaped indentations 72, which engage similarly shaped buckles 18 to allow limited rotation of the buckles 18, as explained in more detail below.

Downwardly-projecting tabs 74L, 74R extend from the lateral walls 68, 70, respectively, and each of these tabs 74L, 74R defines a series of substantially vertically aligned, oval-shaped through openings 76, 78, 80 surrounded by raised inserts 81 (See FIG. 5), similar to the raised inserts 59 described with respect to the range-of-motion locks 22 of FIG. 6A. In this instance, of the three openings 76, 78, 80, only the raised insert 81 surrounding the middle opening 78 has both upper and lower raised flanges 82, 84 (See also FIG. 3). The raised insert 81 surrounding the upper opening 76 has only an upwardly-extending raised flange 86. There are no raised flanges at the lower opening 80.

As with the range-of-motion locks 22, these raised flanges 82, 84, 86 have a tapered outer surface and are relatively flexible to allow them to be deformed far enough to snap through the corresponding openings 48, 50 in the medial shell 14 in order to releasably lock onto the medial shell 14. It should also be noted that there are outward projections on the raised flanges 82, 84, 86 which permit them to be grasped to flex the flange for removal of the upper shell 16 from the medial shell 14.

Of course, other snap-fit arrangements could be used instead, or other known types of connecting mechanisms could be used.

While the brace is being worn, the wearer's foot and leg also tend to keep the tabs 74R, 74L of the upper shell 16 pressed outwardly toward the medial shell 14 and the range-of-motion locks 22 pressed outwardly toward the medial shell 14 and foot shell 12, thereby keeping the range-of-motion locks 22 and the upper shell 16 engaged and secured. Only when the wearer removes the brace and presses on the outward projections of the flanges can he disengage the range-of-motion locks 22 or the upper shell 16.

Figure 3:
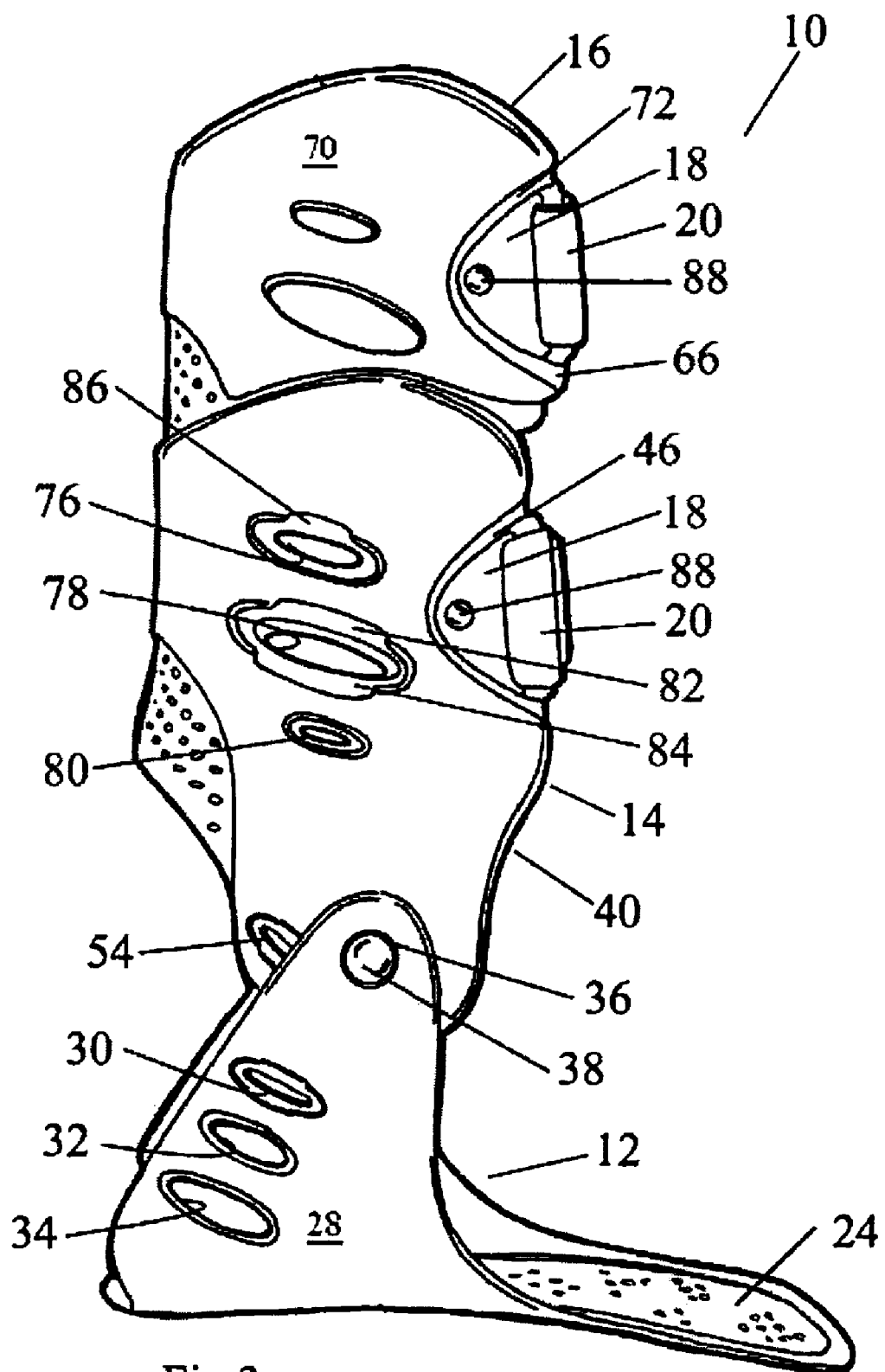
FIG. 3 is a side view of the ankle brace of FIG. 1.

Referring now to FIGS. 2 and 3, the buckles 18 are triangularly shaped to conform generally to the similarly shaped indentations 46, 72 in the outer surface of the medial shell 14 and upper shell 16, respectively. The buckles 18 are rotatably secured to their respective shells 14, 16 with rivets 88, which allow rotation of the buckles 18 about the axes of the rivets 88. However, the rotation of the buckle 18 is limited, or confined, to the area defined by the indentations 46, 72. Since the indentations 46, 72 are slightly larger than the buckles 18 (See FIG. 3), the buckles 18 are able to rotate within a desired range before abutting the sides of the indentations. The range of rotation of the buckle relative to its respective shell preferably is less than 45 degrees, more preferably less than fifteen degrees, and in this case less than ten degrees, to allow the strap 20 to efficiently fit the anatomy of the lower leg while still providing sufficient support and stability.

Of course, the buckle 18 need not be triangularly shaped, nor do the indentations 46, 72 need to be similarly shaped to the buckles 18 in order to provide some kind of stops that limit the rotation of the buckles 18 to a desired or preferred degree of rotation. For example, the stops could be simple projections which extend outwardly from the shells without recessing the buckles.

The straps 20 are secured to the buckles 18 by passing the straps 20 through slotted openings 92 in the buckles 18, as is well known in the art.

Figure 2A:
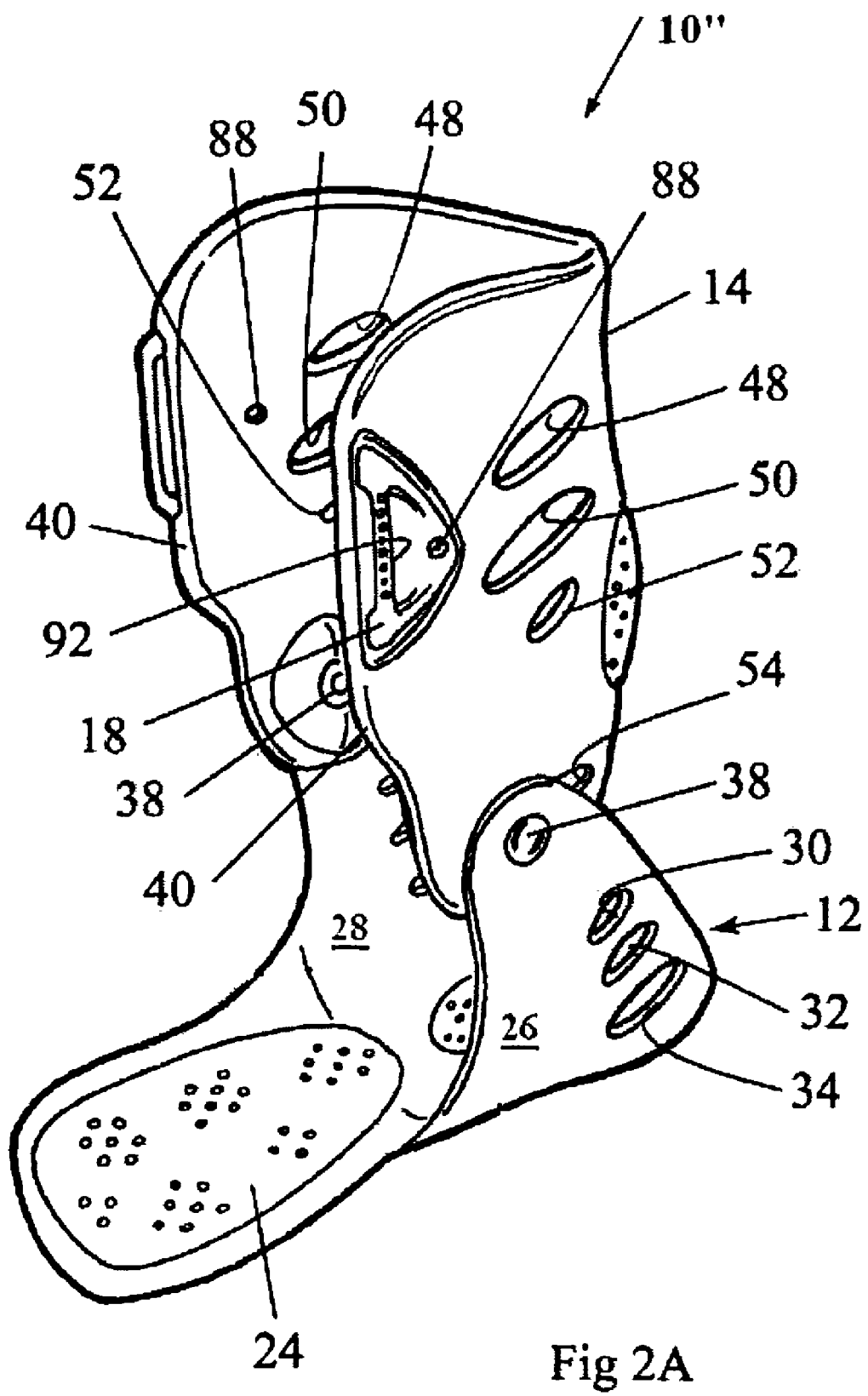
FIG. 2A is a perspective view of a "basic" brace (with the strap removed for clarity), similar to that of FIG. 1 but without the upper extension shell and without the Range-Of-Motion lock.

When the brace 10 is used without the upper extension shell 16 and without the range-of-motion locks 22, it functions as a "basic" pivoting brace 10", as depicted in FIG. 2A. This "basic" brace 10" is designed to be worn during normal athletic activities to prevent an ankle injury, so it is smaller in scale, and provides support without unduly restricting mobility.

Figure 4:
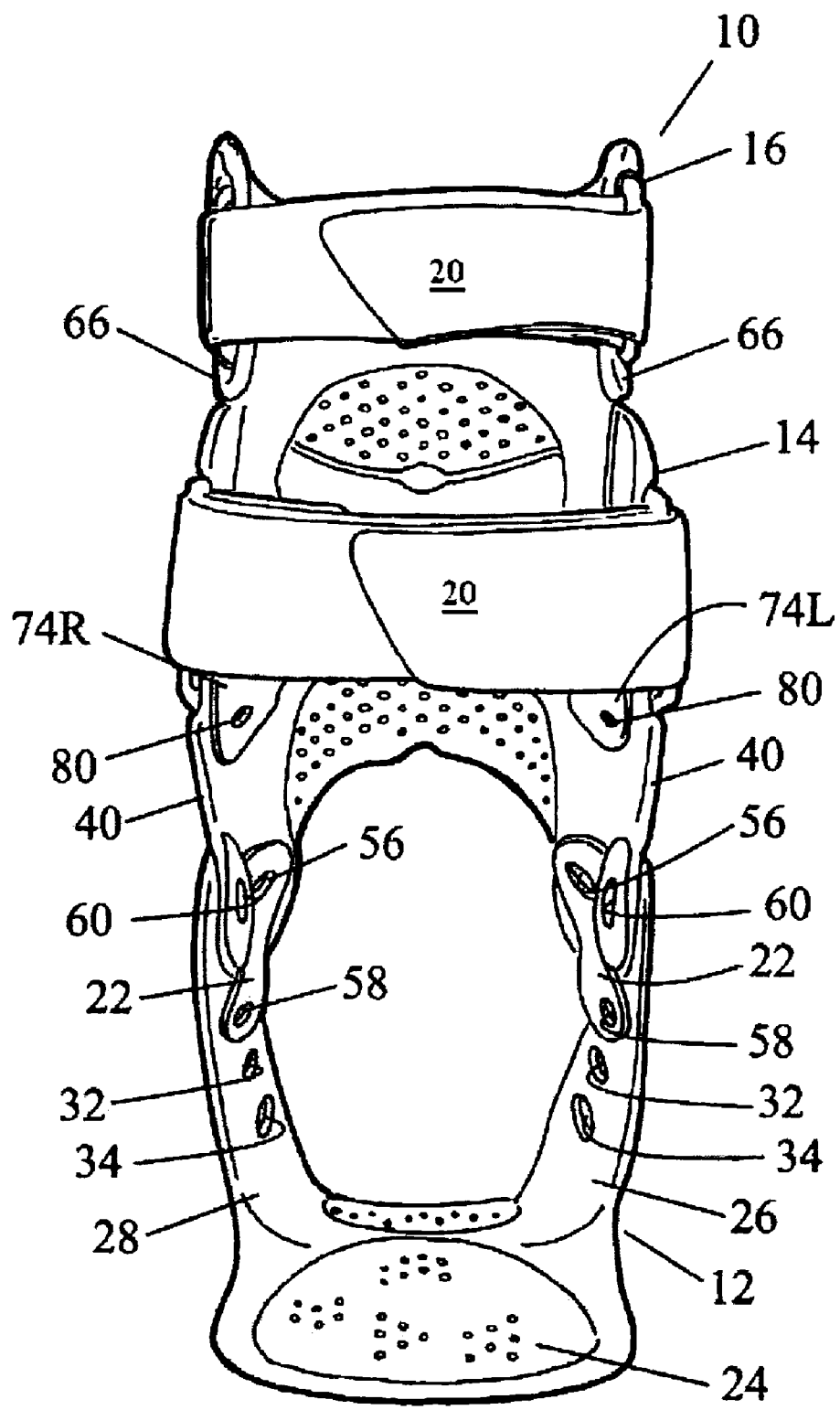
FIG. 4 is a front view of the ankle brace of FIG. 1.

As can be appreciated in FIGS. 3 and 4, the range-of-motion locks 22 may be added to the "basic" brace 10" to releasably fix, or lock, the foot shell 12 and the medial shell 14 to prevent pivotal motion (motion in the forward and aft directions) between these two shells 12, 14. As has been described above, the flanges 61, 62 and inserts 59 of the range-of-motion locks 22 are inserted through their respective openings 30 in the foot shell 12 and openings 54 in the medial shell 14. This locks the foot shell 12 in a neutral position relative to the medial shell 14, preventing the brace 10 from pivoting about the axes defined by the rivets 38 joining these two shells 12, 14.

Adding the left and right range-of-motion locks 22 to the "basic" brace fixes the brace 10 in a neutral position to act as a splint. This splinting effect immobilizes the ankle, which is recommended for acute ankle injuries for the first 24 to 48 hours after the injury. When the swelling and pain have decreased to a point that rehabilitation can start, the range-of-motion locks 22 can be removed from the brace 10, allowing full plantar and dorsiflection of the ankle. Should immobilization be needed again, the range-of-motion locks 22 can be reattached.

Similarly, the upper extension shell 16 may also be releasably attached to the "basic" brace 10" as has already been described. Attaching the upper extension shell 16 to the basic brace makes the brace 10 taller and thereby provides more leverage to help gain additional stability to improve ankle support. The elongated brace 10 with the upper extension 16 is also more rigid, which also adds to the support and stability of the brace 10.

Normally, when an ankle is severely injured, the brace will be used in the form shown in FIG. 1, with the upper extension 16 and range-of-motion locks 22 installed. Then, as the swelling and pain subside, the range-of-motion locks 22 are removed to permit flexing of the ankle. Later, as the ankle heals further, the upper extension 16 is removed, and the brace is used in the form shown in FIG. 2A.

To remove the upper extension shell 16 from the brace 10, one need only squeeze together the flanges 82, 84 of the middle opening 78 and push the flanges out of the opening 50 in the medial shell 14, pushing the tabs 74L, 74R toward the inside of the brace 10. The lowermost raised insert 81 immediately exits its corresponding opening 52 in the medial shell 14 and, as the tabs 74L, 74R pull away from the medial shell 14, they hinge inwardly until the uppermost flange 86 also disengages from its corresponding upper opening 48 of the medial shell 14, and the upper extension shell 16 is released.

Figure 7:
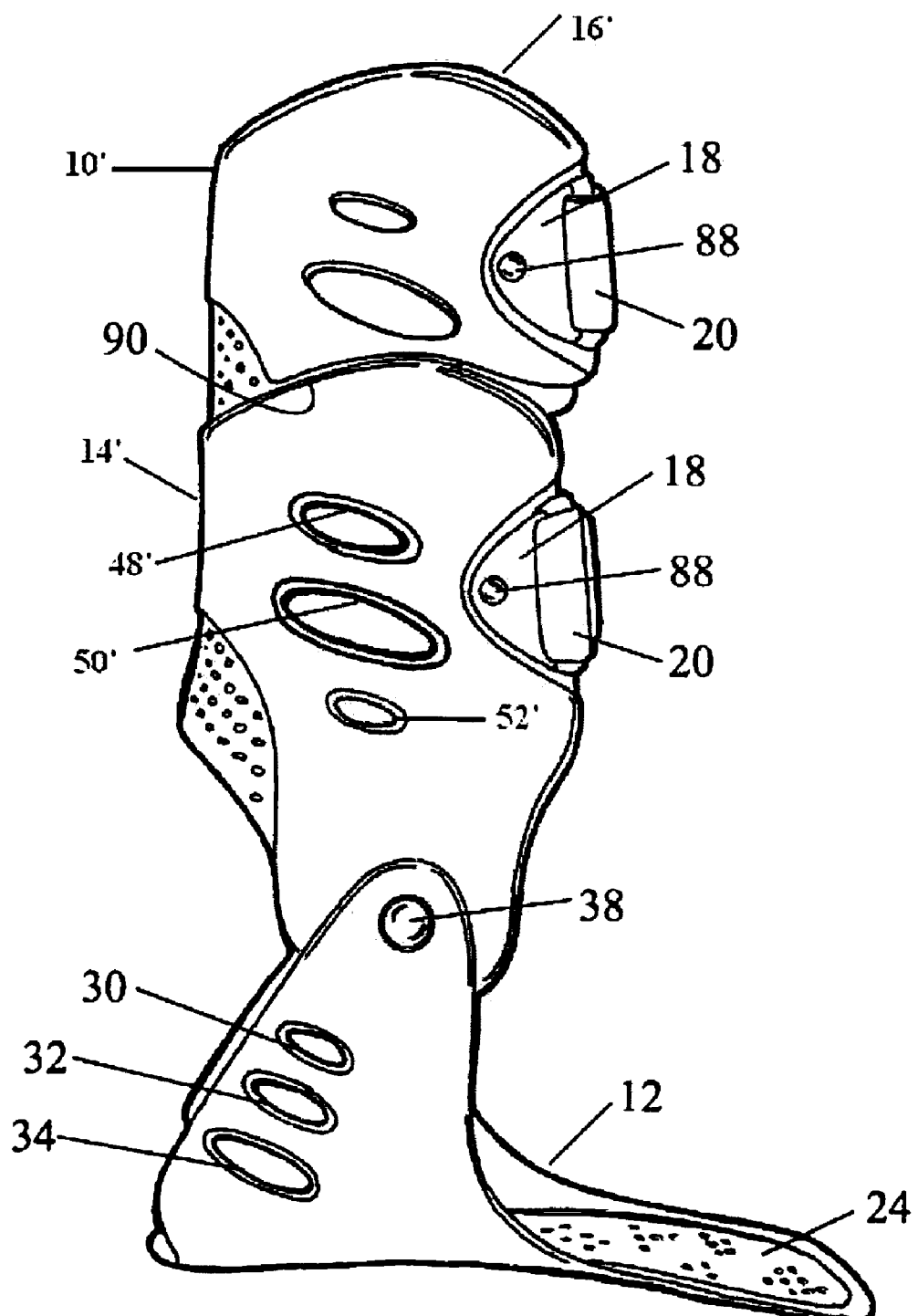
FIG. 7 is a side view of another embodiment of an ankle brace made in accordance with the present invention.
Figure 8:
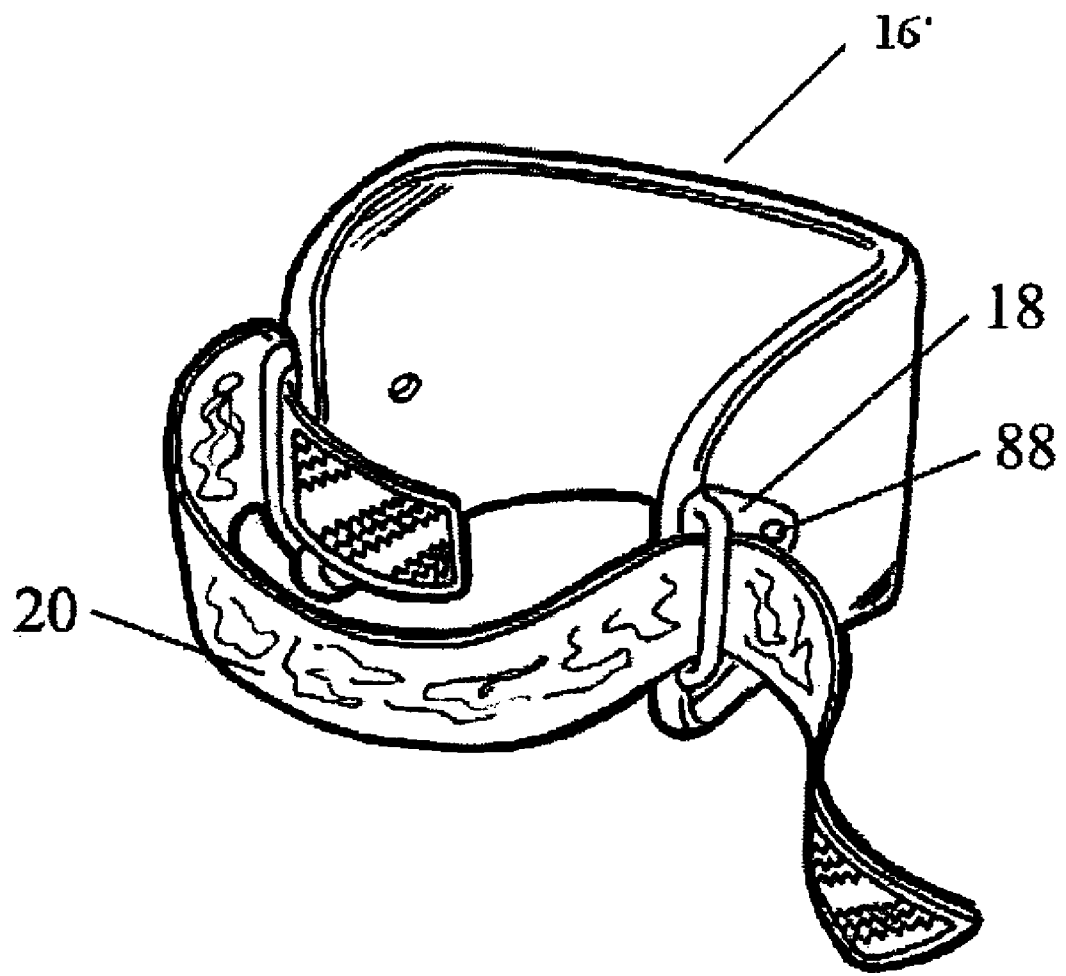
FIG. 8 is a perspective view of the upper extension shell of the ankle brace of FIG. 7.

FIGS. 7 and 8 depict an alternative embodiment of an ankle brace 10' made in accordance with the present invention. The main difference between this embodiment 10' and the previously described embodiment 10 is that the upper extension shell 16' in this embodiment 10' is molded as one piece with the medial shell 14'. An indented cutting guide 90 is molded into the shell, serving as a demarcation between the upper extension shell 16' and the medial shell 14' and showing where the user may cut the shell to separate the upper extension shell 16' from the medial shell 14', if desired, to achieve the "basic" brace 10". Alternatively, the cutting guide could be a decal, a marking, or some other indicator applied to the shell. Of course, in this embodiment, once the upper extension shell 16' has been cut away from the medial shell 14', there is no provision for reattaching it. However, there are through openings 48', 50', 52' in the medial shell 14' which may be used to attach an upper extension shell 16 (as shown in FIG. 5) after the original upper extension shell 16' has been cut off, as has already been described. Alternatively, a connector similar to the range-of-motion locks 22 could be used to snap into openings in the upper shell 16' and the medial shell 14' to re-connect them.

This brace 10' also differs from the previous brace 10 in that it has no provision for a range-of-motion lock 22 to restrict rotation of the foot shell 12 relative to the medial shell 14'. However, it would be obvious to those skilled in the art to provide the through opening 54 in the medial shell 14' of FIG. 7 such that the range-of-motion lock 22 also may be used in this embodiment 10'.

It should also be noted that the range-of-motion locks need not be designed to completely prevent relative rotation. They could, instead, provide some "slop" between the inserts 59 and the respective openings into which they are inserted in order to permit some limited amount of relative motion.

While the embodiments described above show simple means for releasably securing an upper extension shell to a medial shell, as well as means to lock the foot shell to the medial shell, various other mechanisms, such as Velcro™ (hook and loop type) fasteners, alternatively could be used to accomplish these tasks. Also, while they are used on a particular brace design, these features could be used on other brace designs as well. It will be obvious to those skilled in the art that various modifications may be made to the embodiments described above without departing from the scope of the invention as claimed.

What is claimed is:

1. An ankle brace, comprising:
a foot shell including a base for extending beneath the foot and left and right side portions extending upwardly from the base;
a medial shell including left and right lateral walls connected to said left and right side portions of said foot shell, respectively;
an upper extension shell secured to and projecting upwardly from said medial shell along said left and right lateral walls while having demarcations defining the upper extension shell as being separate from the medial shell, wherein each of said medial shell and said upper extension shell includes a posterior portion integral with and connecting its respective lateral walls; and
means for removing said upper extension shell from said medial shell.

2. An ankle brace, comprising:
a foot shell including a base for extending beneath the foot and left and right side portions extending upwardly from the base;
a medial shell including left and right lateral walls connected to said left and right side portions of said foot shell, respectively;
an upper extension shell secured to and projecting upwardly from said medial shell along said left and right lateral walls while having demarcations defining the upper extension shell as being separate from the medial shell; and
means for securing and removing said upper extension shell from said medial shell, wherein said means includes snap-fitting said upper extension shell to said medial shell at a plurality of separate upper positions and lower positions.

3. An ankle brace as recited in claim 2, wherein said left and right lateral walls of said medial shell are pivotably connected to the left and right side portions of the foot shell for pivoting about a pivot axis.

4. An ankle brace as recited in claim 3, wherein said snap-fitting means includes said medial shell defining elongated openings and said upper extension shell including inserts that snap-fit into said elongated openings.

5. An ankle brace as recited in claim 4, and further comprising an elongated range-of-motion restrictor having an upper securement point secured to said medial shell and a lower securement point secured to said foot shell.

6. An ankle brace, comprising:
a foot shell including a base for extending beneath the foot and left and right side portions extending upwardly from the base;
a medial shell including left and right lateral walls connected to said left and right side portions of said foot shell, respectively;
an upper extension shell secured to and projecting upwardly from said medial shell along said left and right lateral walls while having demarcations defining the upper extension shell as being separate from the medial shell, wherein said left and right lateral walls of said medial shell are pivotably connected to the left and right side portions of the foot shell for pivoting about a pivot axis;
means for removing said upper extension shell from said medial shell, wherein said means includes said medial shell defining elongated openings and said upper extension shell including inserts that snap-fit into said elongated openings; and
an elongated range-of-motion restrictor having an upper securement point secured to said medial shell and a lower securement point secured to said foot shell;
wherein said upper securement point includes an upper insert, which is snap-fit into an opening in said medial shell, and said lower securement point includes a lower insert which is snap-fit into an opening in said foot shell.

7. An ankle brace as recited in claim 6, wherein said upper and lower inserts are located to the rear of said pivot axis.

8. An ankle brace, comprising:
a foot shell including a base for extending beneath the foot and left and right side portions extending upwardly from the base;
a medial shell including left and right lateral walls connected to said left and right side portions of said foot shell, respectively;

an upper extension shell secured to and projecting upwardly from said medial shell along said left and right lateral walls while having demarcations defining the upper extension shell as being separate from the medial shell; and means for removing said upper extension shell from said medial shell;

wherein said upper extension shell is integrally molded to the medial shell and said means for removing includes a cutting guide at the demarcation between said medial shell and said upper extension shell.

9. An ankle brace as recited in claim 8, wherein said cutting guide is an indentation molded into said upper shell and said medial shell and forming said demarcation.

10. An ankle brace, comprising:

a foot shell including a base for extending beneath the foot and left and right side portions extending upwardly from the base;

a medial shell including left and right lateral walls connected to said left and right side portions of said foot shell, respectively;

an upper extension shell secured to and projecting upwardly from said medial shell along said left and right lateral walls while having demarcations defining the upper extension shell as being separate from the medial shell;

means for removing said upper extension shell from said medial shell; and further comprising at least one buckle pivotably attached to said medial shell; and stops on said medial shell which limit the range of rotation of said buckle to less than 45 degrees.

11. An ankle brace as recited in claim 10, wherein said stops limit the range of rotation of said buckle to less than fifteen degrees.

12. An ankle brace as recited in claim 11, wherein there are two of said buckles and two corresponding sets of stops, one buckle and set of stops on the left side and one buckle and set of stops on the right side of said medial shell.

13. An ankle brace as recited in claim 12, wherein there are additional left and right buckles and corresponding sets of stops on said upper extension shell.

14. An ankle brace, comprising:

a foot shell including a base for extending beneath the foot and left and right side portions extending upwardly from the base;

a medial shell including left and right lateral walls; and at least one buckle pivotably mounted on one of said left and right lateral walls, wherein said shell defines stops that limit the range of pivoting motion of said buckle to less than 45 degrees.

15. An ankle brace as recited in claim 14, wherein said shell defines a recess that receives said buckle, and said recess has sides which define said stops.

16. An ankle brace as recited in claim 15, wherein said recess has a generally triangular shape and said buckle has a corresponding generally triangular shape.

17. An ankle brace, comprising:

a foot shell including a base for extending beneath the foot and left and right side portions extending upwardly from the base;

a medial shell having left and right lateral walls pivotably connected to the left and right side portions of the foot shell, respectively, for movement about a pivot axis; and an elongated range-of-motion restrictor releasably secured to said medial shell at an upper point and secured to said foot shell at a lower point, wherein said restrictor is secured by a first snap-fit connection at said upper point and by a separate snap-fit connection at said lower point.

18. An ankle brace as recited in claim 17, wherein said upper and lower points are rearward of said pivot axis.

* * * * *